United States Patent [19]
Hayek

[11] Patent Number: 5,988,166
[45] Date of Patent: *Nov. 23, 1999

[54] VENTILATOR APPARATUS

[75] Inventor: Zamir Hayek, London, United Kingdom

[73] Assignee: Dranez Anstalt, Liechtenstein, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/750,179

[22] PCT Filed: May 31, 1995

[86] PCT No.: PCT/GB95/01248

§ 371 Date: Apr. 10, 1997

§ 102(e) Date: Apr. 10, 1997

[87] PCT Pub. No.: WO95/32753

PCT Pub. Date: Dec. 7, 1995

[30] Foreign Application Priority Data

Jun. 1, 1994 [GB] United Kingdom .................. 9410935

[51] Int. Cl.⁶ .................................. A61M 16/00

[52] U.S. Cl. ................ 128/205.26; 128/202.12; 128/204.18; 128/204.24; 128/205.24; 601/41; 601/48

[58] Field of Search .................. 128/204.18, 204.21, 128/204.23, 202.12, 205.26, 204.24, 205.24; 601/41, 48

[56] References Cited

U.S. PATENT DOCUMENTS

| Re. 20,226 | 1/1937 | Drinker et al. |
|---|---|---|
| 2,875,946 | 3/1959 | Tunnicliffe et al. |
| 2,918,917 | 12/1959 | Emerson .................................. 601/41 |
| 4,155,356 | 5/1979 | Venegas .................................. 601/41 |
| 4,265,237 | 5/1981 | Schwanbom et al. ............. 128/204.24 |
| 4,397,306 | 8/1983 | Weisfeldt et al. ........................ 601/41 |
| 4,770,165 | 9/1988 | Hayek . |
| 4,815,452 | 3/1989 | Hayek . |
| 4,881,527 | 11/1989 | Lerman . |
| 4,930,498 | 6/1990 | Hayek . |
| 5,076,259 | 12/1991 | Hayek . |
| 5,359,999 | 11/1994 | Kinsman ............................ 128/204.21 |
| 5,573,498 | 11/1996 | Hayek . |

FOREIGN PATENT DOCUMENTS

| 192337 | 8/1986 | European Pat. Off. ....... A61H 31/02 |
|---|---|---|
| 978758 | 4/1951 | France . |
| 87/04615 | 8/1987 | WIPO ........................... A61H 31/02 |
| 91/11166 | 8/1991 | WIPO .................................... 601/41 |

*Primary Examiner*—John G. Weiss
*Assistant Examiner*—V. Srivastava
*Attorney, Agent, or Firm*—Pillsbury Madison & Sutro LLP

[57] ABSTRACT

Ventilator apparatus for ventilating the lungs of a patient comprises a source of as pressure to be applied internally or externally to a patient's lungs. The alternating pressure has a complex waveform deconstructable into a large amplitude waveform of a first frequency which may be produced by a blower (18) and a valve (10) and a lower amplitude waveform of a higher frequency which may be produced by a second blower and valve unit (4).

20 Claims, 4 Drawing Sheets

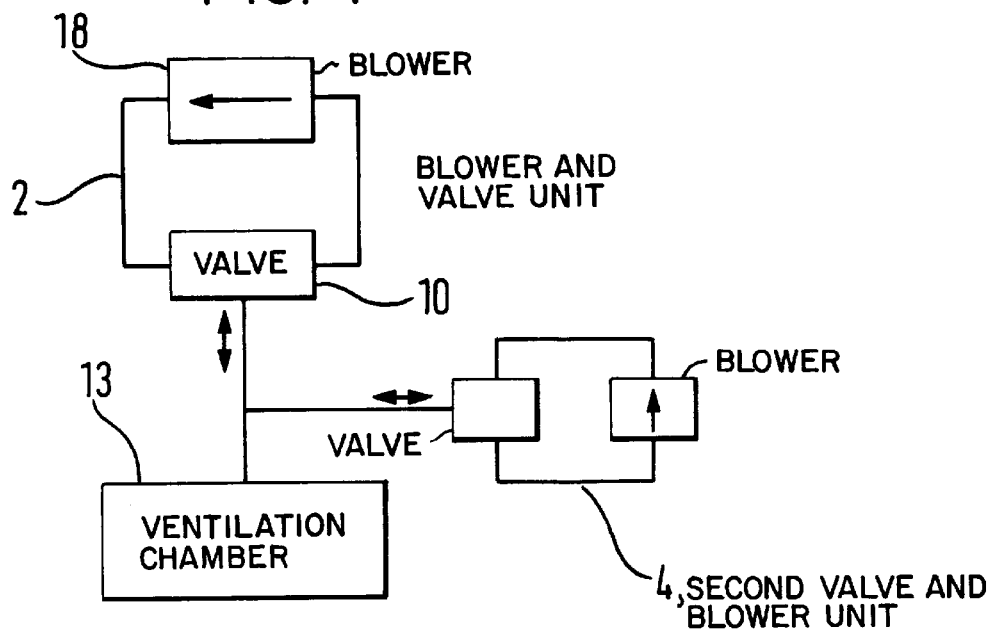
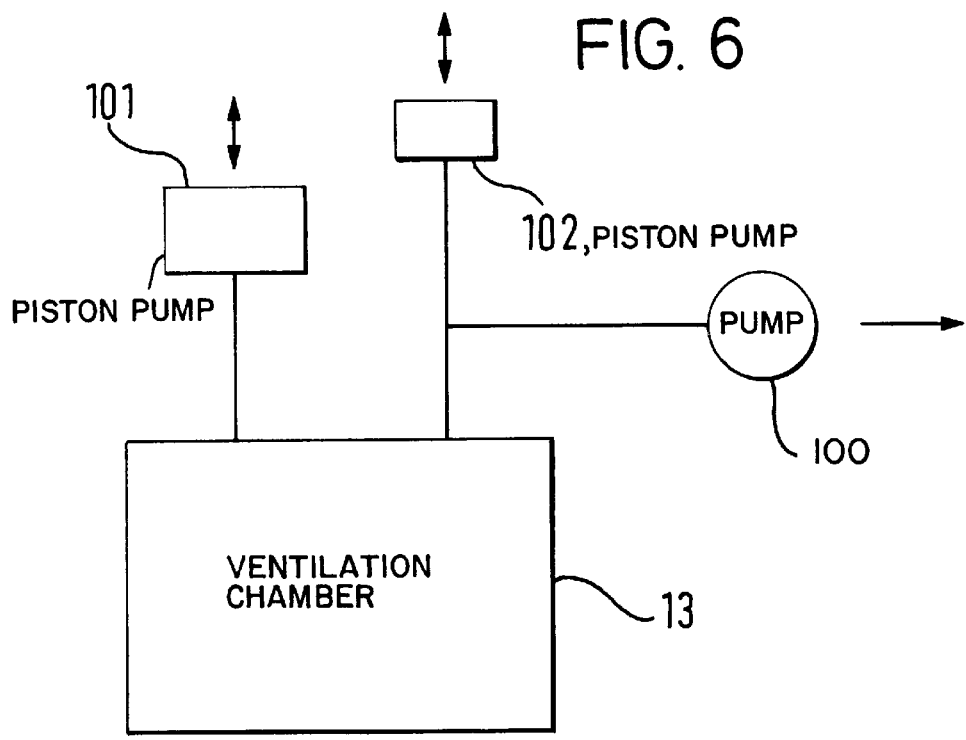

VENTILATOR APPARATUS

This application is the national phase of international application PCT/GB95/01248 filed May 31, 1995 which designated the U.S.

BACKGROUND OF INVENTION

The present invention relates to apparatus for assisting or producing ventilation of the lungs of a patient. Such apparatus may broadly be divided into two types, namely internal and external.

Internal ventilator apparatus directs a flow of breathable gas into the lungs of a patient via a face mask or via an intubation. An alternating gas pressure is employed to produce a tidal flow of gas into and out of the patient's lungs.

External ventilator apparatus comprises some form of chest enclosure, which may cover just the chest or even the whole of the patient below the neck. Alternating gas pressure is applied to the interior of the enclosure to produce compression and expansion of the chest and hence to produce a tidal flow of air into and out of the lungs. Generally, no intubation is needed where external ventilation is used.

The application of pressure to the chest by external ventilation can under certain circumstances cause cardiac stimulation of the kind used when resuscitating a patient in cardiac arrest. Also, the induced chest movement may in some cases be physio-therapeutic. External ventilation can be used to produce cardiac stimulation or for physiotherapy, even where there is no clinical need to ventilate the patient. External ventilators to be used for such purposes are included herein within the term "ventilator apparatus".

Many different regimes of alternating pressure have been proposed both for internal and for external ventilation.

Thus, traditionally, internal ventilation involves the application of alternating gas pressure at a frequency similar to that of natural breathing. However, it has been proposed to employ much higher frequencies in so-called high frequency positive pressure ventilation. A drawback of internal ventilation is that it produces a decrease in cardiac output and it needs intubation with its known complications.

External ventilation has also traditionally been carried out at normal breathing frequency, but in EP-A-0192337 there is disclosed a substantially more beneficial regime in which ventilation is carried out using a relatively high frequency alternation of gas pressure about a negative baseline. This technique is proving to have very substantial clinical benefits.

BRIEF SUMMARY OF THE INVENTION

I have now discovered that both internal and external ventilation regimes can be improved by superimposing on the normal alternating gas pressure employed a higher frequency component. This can reduce the pressure needed for ventilation, reducing barotrauma, and can alleviate the tendency of internal ventilation to produce depression of cardiac output and provide improved cardiac stimulation by external ventilation, as well as producing beneficial physiological changes in the lungs of patients with ARDS (adult respiratory distress syndrome) or other "sick lung" conditions. It also can increase the physiotherapeutic effect obtainable with external ventilation, leading to improved clearance of mucus and liquid from the lungs of the patient.

Accordingly, the present invention provides ventilator apparatus for assisting or producing ventilation of the lungs of a patient, comprising a source of alternating gas pressure, means for applying said alternating gas pressure internally or externally to the lungs of a patient to produce ventilation, and further comprising means for superimposing on said alternating gas pressure a higher frequency component of alternating gas pressure.

Preferably, the amplitude of said higher frequency component is no more than one third of the amplitude of the said alternating gas pressure without said higher frequency component, e.g. no more than one fourth of the amplitude of said alternating gas pressure without said higher frequency component, and most preferably from one fourth to one tenth of the amplitude of said alternating gas pressure without said higher frequency component. It may for instance be from −2 to +2 cm −H$_2$O (amplitude 4 cm −H$_2$O) to −10 to +10 cm H$_2$O (amplitude 20 cm H$_2$O); e.g. +5 to −5 cm H$_2$O, whilst the main alternation in gas pressure has an amplitude of from 25 to 80 cm H$_2$O, more preferably 30 to 40 cm H$_2$O.

Preferably the frequency of said higher frequency component is at least three times the frequency of said alternating gas pressure, e.g. from 5 to 30 times the frequency of said alternating gas pressure, most suitably about ten times the frequency of said alternating gas pressure. It may for instance have a frequency of from 90 cycles/min (1.5 Hz) to 50 Hz, e.g. 3 to 20 Hz. The main ventilating alternating gas pressure may hve a frequency of from 8 cycles/min (0.13 Hz) to 16 Hz, preferably from 1 to 6 Hz.

Said means for applying said alternating gas pressure may comprise an airway for intubation of a patient or may comprise an enclosure for application over at least the chest of a patient.

The apparatus preferably further includes means for producing a negative base line pressure for said alternating gas pressure. Preferably, the apparatus is in accordance with the teachings of EP-A-0192337.

Said means for superimposing a higher frequency component of alternating gas pressure may comprise a source of positive pressure, a source of negative pressure, and a fluid control valve connected between the source of positive fluid pressure, the source of negative fluid pressure and a conduit connected to said means for applying said alternating gas pressure, said valve comprising a valve body having a first subsidiary port connected to said source of positive pressure, a second subsidiary port connected to said source of negative pressure and a main port connected to said conduit, and a valve mechanism operable selectively to connect said first subsidiary port to said main port whilst blocking connection between said second subsidiary port and said main port and also to connect said second subsidiary port and said main port whilst blocking connection between said first subsidiary port and said main port, said valve further including a second valve mechanism co-operating with said first valve mechanism and serving to open a temporary connection to the exterior of the valve from whichever of the first and second subsidiary ports is blocked off from the main port.

Valve arrangements of this type are described in GB93106490.

Preferably, the first valve mechanism comprises a valve seat in said valve body having openings therein communicating with respective ones of said first and second subsidiary ports and a shutter member having a sealing face overlying said valve seat and being moveable between a first range of positions in which the opening of openings in said valve seat communicating with said first subsidiary port is or are opened and said opening or openings communication with said second subsidiary port is or are closed and a second range of positions in which the opening or openings of said valve seat communication with said second subsidiary port is or are opened and said opening or openings in said valve seat communicating with said first subsidiary port is or are closed.

Preferably, the second valve mechanism comprises a second valve seat in said valve body having openings therein communicating with respective ones of said first and second subsidiary ports and a shutter member having a sealing face overlying said valve seat and being moveable between a first range of positions in which the opening or openings in said valve seat communicating with said second subsidiary port is or are opened and said opening or openings communicating with said first subsidiary port is or are closed and a second range of positions in which said opening or openings communicating with said first subsidiary port is or are opened and said opening or openings connected with said second subsidiary port is or are closed, said first shutter member and said shutter member being linked together to move in synchrony between their said first and second ranges of position.

The first and second valve mechanism shutter members may be rotary shutter members each pivotable about an axis to move between said first and second ranges of position.

The apparatus may comprise a rotatable shaft member defining said axis and carrying both said first and said second valve mechanism shutter members thereon.

The first and second valve shutter members may be positioned 180° out of phase with respect to one another.

The first valve mechanism may be operable in a progressive manner so as to allow a user to select from within a range the maximum effective cross-sectional area of the path of communication opened between the main port and each of the first and second subsidiary ports during operation of the valve.

Between the position of adjustment of the first valve mechanism which connects the subsidiary port to the main port and the position of operation of the first valve mechanism which connects the second subsidiary port to the main port, there may be a position of operation in which neither the first subsidiary port nor the second subsidiary port is connected to the main port.

The rotary shutter members may be connected to an electronic stepper motor for control of their position.

Said means for superimposing a higher frequency alternating gas pressure may alternatively comprise a piston pump or bellows pump.

The invention will be further described and illustrated with reference to the accompanying drawings showing preferred embodiments of the invention, in which:

LIST OF DRAWINGS

FIG. 1 is a schematic diagram of a first preferred embodiment;

FIG. 6 is a schematic diagram of a second preferred embodiment according to the invention.

DETAILED DESCRIPTION

As shown in FIG. 1, a first embodiment of apparatus according to the invention comprises a ventilator chamber 13 for receiving at least the chest of a patient. The chamber may be of the kind enclosing the front and the back of the patient's chest or may be of the cuirass type in which the ventilator chamber shell fits over the front of the patient's chest only. A main source of alternating pressure in the chamber 13 is a blower and valve unit 2 comprising a blower 18 and a valve 10. The valve and blower unit 2 may be as described in co-pending Application GB 9310649.0. Such a valve and blower unit is illustrated in FIGS. 2 to 5.

Figure 2:
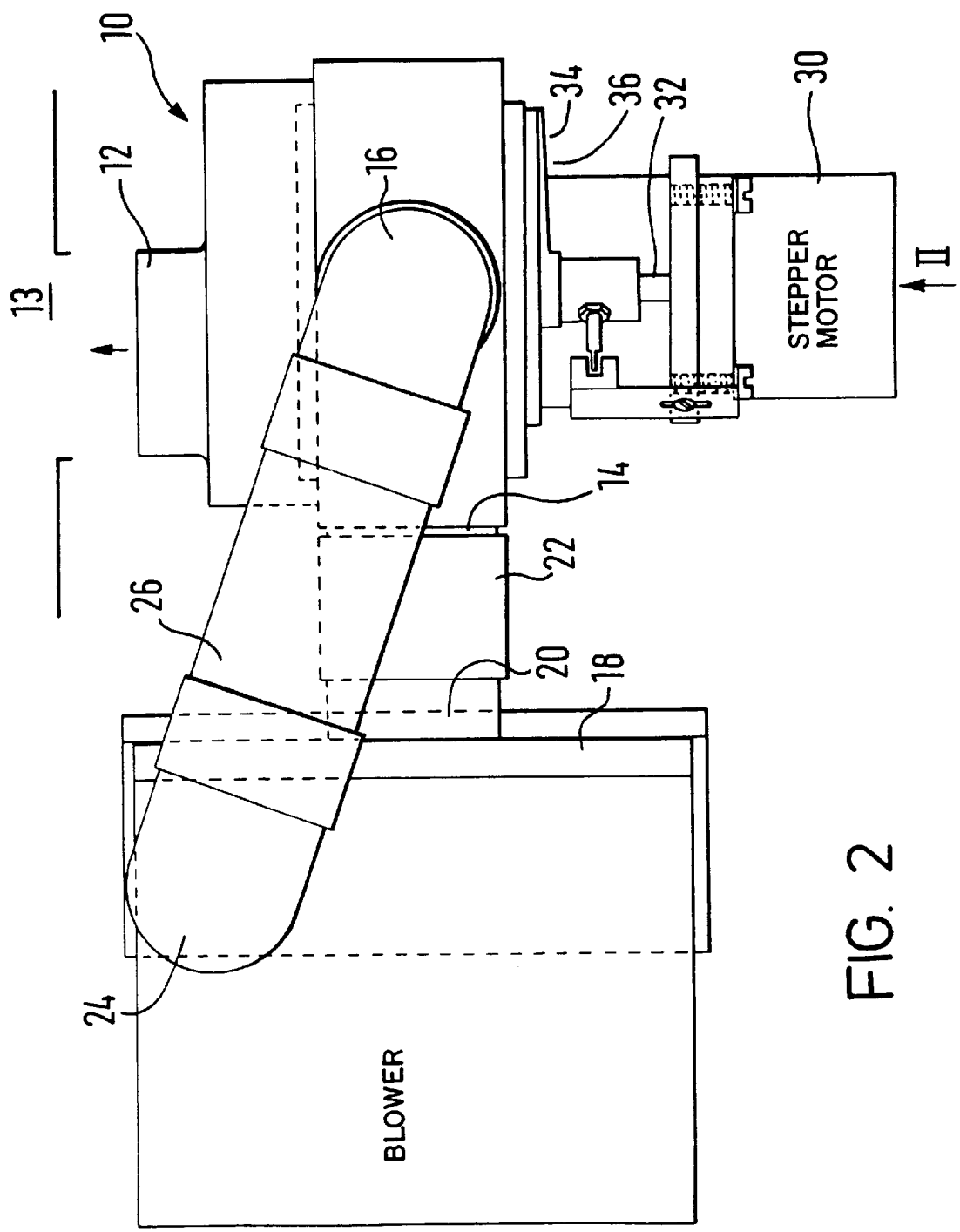
FIG. 2 is a plan view of a valve and blower unit for use in the apparatus of FIG. 1.
Figure 3:
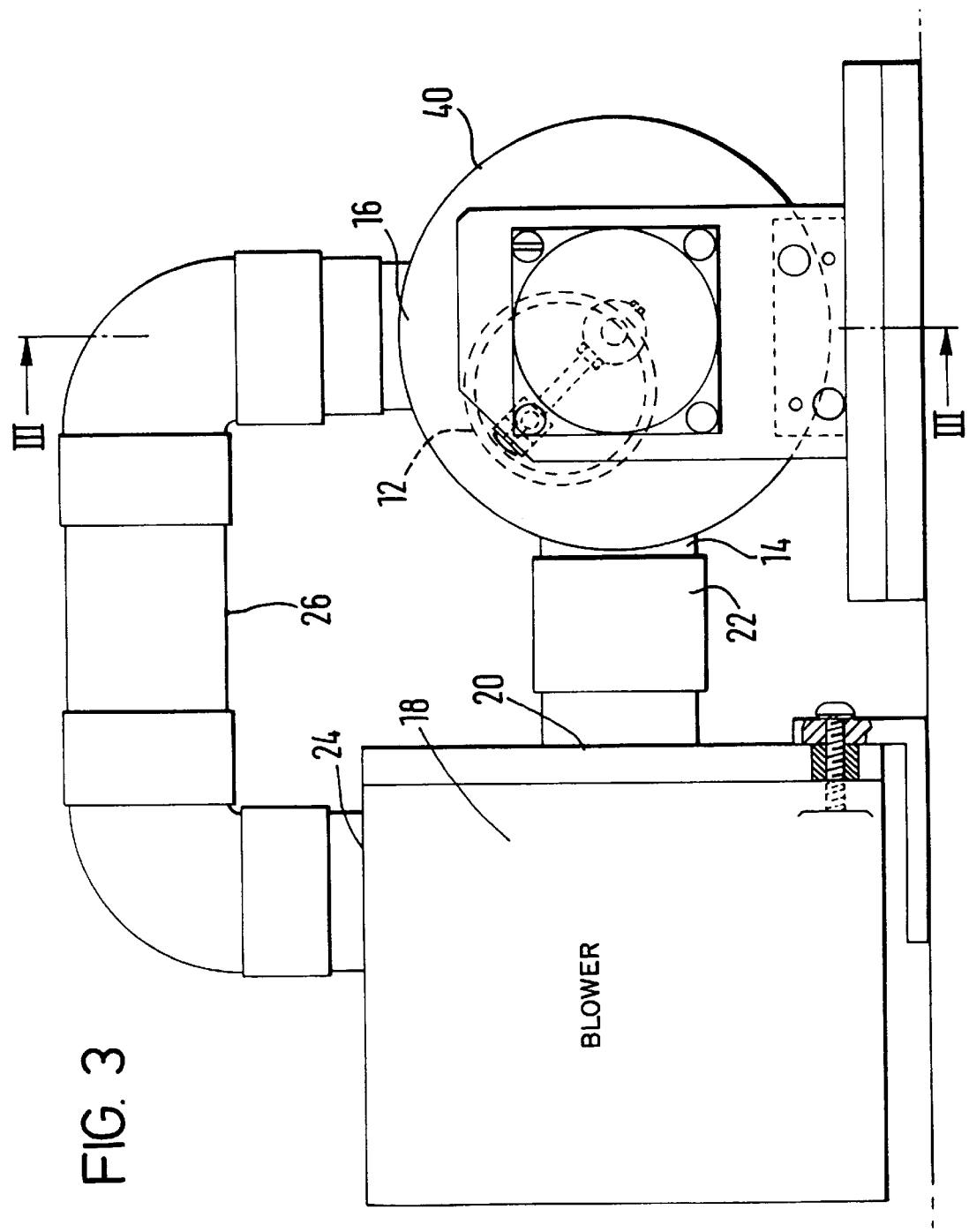
FIG. 3 is a elevation on the line II—II of FIG. 2.

As shown in FIG. 2, a valve 10 according to the invention has a main port 12 communicating with the ventilator enclosure schematically shown at 13 and first and second subsidiary ports 14, 16 providing access to the interior of the valve. A blower 18 has an outlet 28 for air connected via a conduit 22 to subsidiary port 14 of the valve and an inlet 24 for air connected via a conduit 26 to port 16 of the valve. An electronic stepper motor 30 is connected to the valve by a rotatable shaft 32 in a manner described in further detail hereafter to control the action of the valve. By the operation of the stepper motor 30, the main port 12 of the valve is communicated with the outlet 20 for compressed air from the blower and with the inlet 24 to the blower in alternating succession. Third and fourth subsidiary ports 34, 36 communicating with atmosphere are provided in the valve body as further described below.

Figure 4:
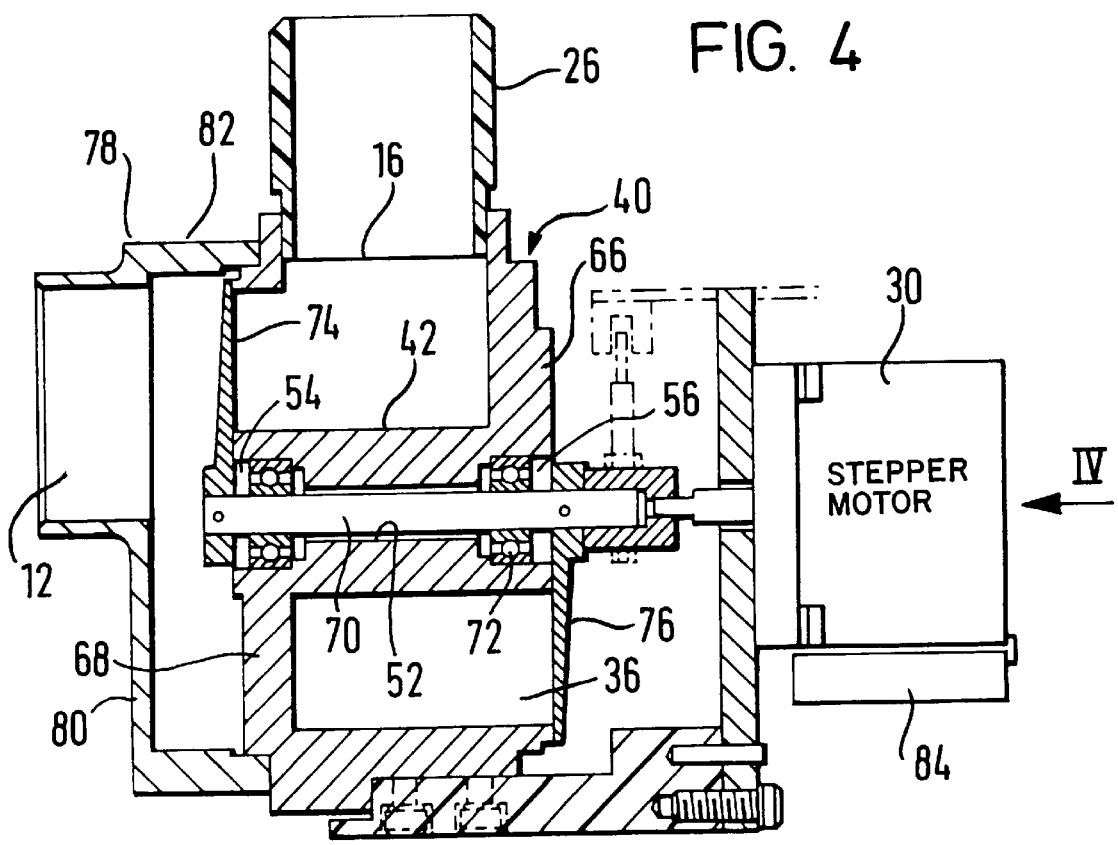
FIG. 4 is a section on the line III—III in FIG. 3.
Figure 5:
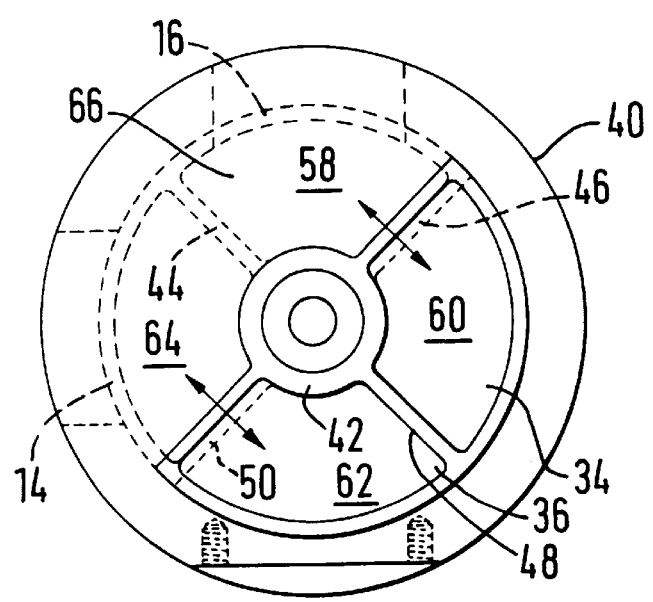
FIG. 5 is a view in the direction of the arrow IV in FIG. 4 of the central body portion of the valve illustrated.

As shown in FIG. 4, the valve 10 in greater detail comprises a main body portion 40 which is generally in the form of a hollow cylinder with a central tubular member 42 supported on the axis thereof by webs 44, 46, 48, 50 (FIG. 5). The tubular member 42 has a bore 52 therethrough which at each end has a wider diameter counter bore 54, 56.

At locations spaced around the exterior of the body 40 by 90° there are provided the subsidiary ports 14, 16. The webs 44–50 divide the interior of the body portion 40 into four quarter-cylindrical segments 58, 60, 62, 64. The webs 48 and 44 are solid whilst the webs 46 and 50 are windowed so that within the hollow cylindrical body portion 40 there is gas communication between the segments 58 and 60 and between 62 and 64 but the segments 64 and 58 are isolated from one another as are the segments 60 and 62.

The face of the body portion 40 seen in FIG. 5 has a semi-circular rear wall 66 covering the segments 58 and 64. At the opposite end of the body portion 40 there is a similar semi-circular wall 68 covering the opposite end of the segments 60, 62. Thus, the semi-circular walls 66 and 68 are 180° out of phase with one another. Four quarter circular windows are thereby provided to the body portion 40, two on the right hand face of the body portion shown in FIG. 4 and two on the left hand face of the body portion shown in FIG. 3. The quarter circular windows in the rear or right hand face of the body portion as shown in FIG. 4 constitute the ports 34 and 36 referred to above.

A shaft 70 extends through bore 52 in the body portion 40 supported upon bearings 72 received in the counter-bores 54, 56. Pinned on the left-hand end (FIG. 4) of the shaft 70 is a first shutter member 74 which takes the form of a semi-circular metal plate. A second similar semi-circular metal plate shutter member 76 is pinned to the shaft 52 adjacent the opposite end of the body portion 40 and is arranged 180° out of phase of the shutter member 74. Thus, the two shutter members can be arranges such that shutter member 74 covers both of the windows out of the left hand end of the body portion 40 in FIG. 4 whilst shutter member 76 simultaneously covers both of the ports 34, 36 at the right hand end of the body portion as shown in FIG. 4. The shaft 52 is connected at its right hand end (in FIG. 4) to the stepper motor 30.

The body of the valve is completed by a front member 78 having a front wall 80 containing the main port 12 located eccentrically thereon and having a circular flange 82 received as a push-fit over a boss on the body portion 40 surrounding the area swept out by rotation of the shutter 74. The port 12 (which is shown slightly out of position in FIG. 4) lies equi-angularly between the subsidiary ports 14 and 16 and hence lies directly over the web 44.

An electronic control circuit 84 is provided for controlling movement of the electronic stepper motor.

The operation of the valve and blower unit embodiment is as follows. Starting from a position in which the two shutter members are positioned totally covering their respective openings in the body portion 40 of the valve, the electronic stepper motor is operated to rotate the shaft 52 and hence the shutter members 74 and 76 by up to a quarter turn so as to uncover the window at the front end of the segment 64 which is thus in communication with the main port 12 so that the main port 12 is communicated with the subsidiary port 14. The shutter member 74 slides in an airtight manner on the front (or left hand in FIG. 4) face of the body portion 40 which constitutes a valve seat for it and with said valve seat constitutes a first valve mechanism.

At the same time, the second shutter member 76 sliding upon the rear (right hand in FIG. 4) face of the body portion 40 which acts as a valve seat uncovers the port 34 which via the window in web 46 communicates the segmental chamber 60 with the segmental chamber 58 which in turn is in communication with the subsidiary port 16. Positive air pressure applied from the blower through its port 20 to the port 14 of the valve is thereby communicated out of the main port 12 of the valve which is in connection with the patient ventilator chamber and the necessary air supply to the negative pressure side of the blower is provided through port 16 and the subsidiary port 34.

The shutter member assembly is rotated back in the opposite direction to carry both shutter members back by up to 180° so that the front shutter member 74 not opens the window at the front of the segmental chamber 58 in the body portion 40 which communicates with the subsidiary port 16 whilst the rear shutter member 76 opens the subsidiary port 36. Positive pressure from the blower entering the valve through the port 14 is now dumped through the subsidiary port 36 while negative pressure from the blower in the form of suction applied at the subsidiary port 16 is communicated through to the main port 12 and hence to the patient ventilation chamber.

By varying the speed of movement of the shutters and the amount of opening of the ports both in the positive and in the negative pressure phases at the main port 12, one can with great flexibility vary the pressure regime applied through the port 12 to a patient ventilator chamber. One may alter the shape of the pressure pulses applied, their duration and their frequency. In particular, one can produce pressure oscillations about a negative pressure baseline in external ventilation and about a positive pressure baseline in internal ventilation.

Sensors may be provided in the apparatus to detect the rotational position of the shaft 52 so as to provide feed-back to the circuitry 84 controlling the motor 30.

As shown in FIG. 1, the apparatus according to the present invention comprises a second valve and blower unit 4 which may resemble valve and blower unit 2 in its construction but it smaller, of less volumetric capacity and adapted to operate at a higher frequency. Thus for instance, whilst the valve and blower unit 2 may be adapted to provide oscillations at a frequency of from 1.5 Hz to 50 Hz, e.g. 3 to 20 Hz, the smaller valve and pump unit 4 is preferably adapted to be set to provide pressure pulses at a frequency of from 5 to 3 times the frequency of the oscillations provided by the valve and pump unit 2 and of an amplitude which is from 0.3 to 0.1 times the amplitude of the oscillations provided by the valve and blower unit 2.

The ventilation enclosure 13 can instead be a face mask or an intubation for internal ventilation.

In an alternative embodiment schematically illustrated in FIG. 6, a negative baseline pressure is established in a ventilator chamber 13 by a constantly acting pump 100 and an oscillating pressure is imposed on the negative baseline pressure in the chamber 13 by a reciprocating bellows unit or piston pump 101. A higher frequency pressure oscillation is imposed by a smaller capacity second bellows unit or second piston pump 102. The amplitudes and frequencies of the oscillations provided by the bellows units or piston pumps 101 and 102 may be as described above in connection with the valve and pump units 2 and 4 in FIG. 1.

Many modifications and variation of the invention as described herein are possible within the scope of the invention.

I claim:

1. Ventilator apparatus for assisting or producing ventilation of the lungs of a patient, comprising:

a source of alternating gas pressure, and means for applying said alternating gas pressure internally or externally to the lungs of a patient to produce ventilation, wherein said source of alternating gas pressure produces a gas pressure ventilation comprising superposed first and second periodic gas pressure variation components, said first periodic gas pressure variation component having a first frequency, and said second periodic gas pressure variation component having a second frequency, which is higher than said first frequency.

2. Apparatus as claimed in claim 1, wherein the amplitude of said higher frequency component is no more than one quarter of the amplitude of the said alternating gas pressure without said higher frequency component.

3. Apparatus as claimed in claim 2, wherein the amplitude of said higher frequency component is no more than one tenth of the amplitude of said alternating gas pressure without said higher frequency component.

4. Apparatus as claimed in claim 3, wherein the amplitude of said higher frequency component is from one tenth to one fiftieth of the amplitude of said alternating gas pressure without said higher frequency component.

5. Apparatus as claimed in claim 1, wherein the frequency of said higher frequency component is at least five times the frequency of said alternating gas pressure.

6. Apparatus as claimed in claim 5, wherein the frequency of said higher frequency component is from 5 to 30 times the frequency of said alternating gas pressure.

7. Apparatus as claimed in claim 6 wherein the frequency of said higher frequency component is about ten times the frequency of said alternating gas pressure.

8. Apparatus as claimed in claim 1 for internal ventilation, wherein said means for applying said alternating gas pressure comprises an airway for intubation of a patient or a face mask.

9. Apparatus as claimed in claim 1 for external ventilation, wherein said means for applying said alternating gas pressure comprises an enclosure for application over at least the chest of a patient.

10. Apparatus as claimed in claim 1, further including means for producing a negative base line pressure for said alternating gas pressure.

11. Ventilator apparatus for assisting or producing ventilation of the lungs of a patient, comprising:

a source of alternating gas pressure, means for applying said alternating gas pressure internally or externally to the lungs of a patient to produce ventilation, and means for superimposing on said alternating gas pressure a higher frequency component of alternating gas pressure, wherein said means for superimposing a higher frequency component of alternating gas pressure comprises a source of positive pressure, a source of negative pressure, and a fluid control valve connected between the source of positive fluid pressure, the source of negative fluid pressure and a conduit connected to said means for applying said alternating gas pressure, said valve comprising a valve body having a first subsidiary port connected to said source of positive pressure, a second subsidiary port connected to said source of negative pressure and a main port connected to said conduit, and a valve mechanism operable selectively to connect said first subsidiary port to said main port whilst blocking connection between said second subsidiary port and said main port and also to connect said second subsidiary port to said main port whilst blocking connection between said first subsidiary port and said main port, said valve further including a second valve mechanism cooperating with said first valve mechanism and serving to open a temporary connection to the exterior of the valve from whichever of the first and second subsidiary ports is blocked off from the main port.

12. Apparatus as claimed in claim 11, wherein the first valve mechanism comprises a valve seat in said valve body having openings therein communicating with respective ones of said first and second subsidiary ports and a shutter member having a sealing face overlying said valve seat and being moveable between a first range of positions in which the opening or openings in said valve seat communicating with said first subsidiary port is or are opened and said opening or openings communicating with said second subsidiary port is or are closed and a second range of positions in which the opening or openings of said valve seat communicating with said second subsidiary port is or are opened and said opening or openings in said valve seat communicating with said first subsidiary port is or are closed.

13. Apparatus as claimed in claim 11, wherein the second valve mechanism comprises a second valve seat in said valve body having openings therein communicating with res-pective ones of said first and second subsidiary ports and a shutter member having a sealing face overlying said valve seat and being moveable between a first range of positions in which the opening or openings in said valve seat communicating with said second subsidiary port is or are opened and said opening or openings communicating with said first subsidiary port is or are closed and a second range of positions in which said opening or openings communicating with said first subsidiary port is or are opened and said opening or openings connected with said second subsidiary port is or are closed, said first shutter member and said second shutter member being linked together to move in synchrony between their said first and second ranges of position.

14. Apparatus as claimed in claim 12, wherein the first and second valve mechanism shutter members are rotary shutter members each pivotable about an axis to move between said first and second ranges of position.

15. Apparatus as claimed in claim 14, comprising a rotatable shaft member defining said axis and carrying both said first and said second valve mechanism shutter members thereon.

16. Apparatus as claimed in claim 14, wherein the first and the second valve mechanism shutter members are positioned 180° out of phase with respect to one another.

17. Apparatus as claimed in claim 11, wherein the first valve mechanism is operable in a progressive manner so as to allow a user to select from within a range the maximum effective cross-sectional area of the path of communi-cation opened between the main port and each of the first and second subsidiary ports during operation of the valve.

18. Apparatus as claimed in claim 11, wherein between the position of adjustment of the first valve mechanism which connects the subsidiary port to the main port and the position of operation of the first valve mechanism which connects the second subsidiary port to the main port, there is a position of operation in which neither the first subsidiary port nor the second subsidiary port is connected to the main port.

19. Apparatus as claimed in claim 14, wherein the rotary shutter members are connected to an electronic stepper motor for control of their position.

20. Ventilator apparatus for assisting or producing ventilation of the lungs of a patient, comprising:

a source of alternating gas pressure, means for applying said alternating gas pressure internally or externally to the lungs of a patient to produce ventilation, and means for superimposing on said alternating gas pressure a higher frequency component of alternating gas pressure, wherein said means for superimposing a higher frequency alternating gas pressure comprises one of a piston pump and a bellows pump.

* * * * *